United States Patent
Gavard Molliard

(10) Patent No.: US 10,434,040 B2
(45) Date of Patent: *Oct. 8, 2019

(54) INJECTABLE STERILE AQUEOUS FORMULATION BASED ON CROSSLINKED HYALURONIC ACID AND HYDROXYAPATITE FOR AESTHETIC USE

(71) Applicant: ANTEIS S.A., Plan-les-Ouates (CH)

(72) Inventor: Samuel Gavard Molliard, Bogève (FR)

(73) Assignee: ANTEIS S.A., Plan-les-Ouates (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/941,735

(22) Filed: Mar. 30, 2018

(65) Prior Publication Data

US 2018/0221255 A1    Aug. 9, 2018

Related U.S. Application Data

(63) Continuation-in-part of application No. 15/913,086, filed on Mar. 6, 2018, which is a continuation of application No. 14/433,927, filed as application No. PCT/EP2013/069874 on Sep. 24, 2013, now abandoned.

(30) Foreign Application Priority Data

Oct. 8, 2012 (FR) ...................... 12 59577

(51) Int. Cl.
| | |
|---|---|
| *A61K 8/02* | (2006.01) |
| *A61K 8/04* | (2006.01) |
| *A61K 8/24* | (2006.01) |
| *A61K 8/73* | (2006.01) |
| *A61Q 19/08* | (2006.01) |

(52) U.S. Cl.
CPC ............ *A61K 8/042* (2013.01); *A61K 8/0241* (2013.01); *A61K 8/24* (2013.01); *A61K 8/735* (2013.01); *A61Q 19/08* (2013.01); *A61K 2800/412* (2013.01); *A61K 2800/54* (2013.01); *A61K 2800/91* (2013.01)

(58) Field of Classification Search
CPC ... A61K 8/02; A61K 8/04; A61K 8/08; A61K 8/24; A61K 8/73
See application file for complete search history.

(56) References Cited

U.S. PATENT DOCUMENTS

| | | |
|---|---|---|
| 5,922,025 A | 7/1999 | Hubbard |
| 8,455,465 B2 | 6/2013 | Gavard Molliard |
| 2010/0004700 A1 | 1/2010 | Alleyne |
| 2011/0201571 A1 | 8/2011 | Gavard Molliard |
| 2012/0108674 A1 | 5/2012 | Gavard Molliard et al. |
| 2012/0238644 A1 | 9/2012 | Gong |
| 2015/0238525 A1 | 8/2015 | Gavard Molliard |

FOREIGN PATENT DOCUMENTS

| | | |
|---|---|---|
| FR | 2938187 | 5/2010 |
| FR | 2945949 | 12/2010 |
| WO | WO9316657 | 9/1993 |
| WO | WO 2004/011053 | 2/2004 |
| WO | WO 2010/052430 | 5/2010 |
| WO | WO 2010/136694 | 12/2010 |

OTHER PUBLICATIONS

Bakos, D., et al., Biomaterials, vol. 20, No. 2, p. 191-195, Jan. 1, 1999.
International Search Report for PCT/EP20131069874 dated May 12, 2014.
Kristoffer Bergman, "Hyaluronan Derivatives and Injectable Gels for Tissue Engineering" Uppsala Universitet, vol. 573, Nov. 14, 2008.
U.S. Appl. No. 16/272,127, Aptissen S.A.

*Primary Examiner* — Zohreh A Fay
(74) *Attorney, Agent, or Firm* — Hueschen and Sage

(57) ABSTRACT

The object of the present invention is an injectable sterile aqueous formulation, ready-to-use, resorbable, used for aesthetic purposes as a particulate, cohesive, viscoelastic gel comprising i) crosslinked hyaluronic acid, or one of its salts, at a concentration of between 0.1% and 4% (mass/volume); the crosslinking carried out providing the possibility of obtaining a gel based on crosslinked hyaluronic acid with a so-called cohesive structure, and ii) hydroxyapatite, at a concentration of between more than 70% and 140% (mass/volume), said hydroxyapatite being in the form of particles with an average size of less than or equal to 200 μm; said injectable sterile aqueous formulation having viscoelastic properties such that tan δ at the frequency of 1 Hz is less than or equal to 0.60.

19 Claims, 1 Drawing Sheet

| Product tested | Observation before agitation | Observation immediately after agitation | Observation after 10 seconds following agitation |
|---|---|---|---|
| Gel B' According to the invention (Example 2) | | | |
| Gel X (Example 2) | | | |
| CMC and hydroxyapatite-based formulation (Example 4) | | | |

INJECTABLE STERILE AQUEOUS FORMULATION BASED ON CROSSLINKED HYALURONIC ACID AND HYDROXYAPATITE FOR AESTHETIC USE

FIELD OF THE INVENTION

The object of the present invention is a ready-to-use resorbable injectable sterile aqueous formulation used for aesthetic purposes as a particulate cohesive viscoelastic gel comprising i) crosslinked hyaluronic acid, or one of its salts, at a concentration of between 0.1% and 4% (mass/volume); the crosslinking carried out providing the possibility of obtaining a gel based on crosslinked hyaluronic acid with a so-called cohesive structure and ii) hydroxyapatite, at a concentration of between more than 70% and 140% (mass/volume), said hydroxyapatite being in the form of particles with an average size of less than or equal to 200 µm; said injectable sterile aqueous formulation having viscoelastic properties such that tan δ at the frequency of 1 Hz is less than or equal to 0.60.

BACKGROUND OF THE INVENTION

Ageing is a natural phenomenon with which any individual is confronted. It is inevitably accompanied by a reduction in the cell activity of the human body.

The most visible signs of age appear on the face: the skin slackens and the first wrinkles appear. Many solutions have been developed for attempting to slow down the occurrence of these signs of age or to repair already established signs.

Among these solutions, mention may be made of a technique which consists of injecting into or under the skin so-called filling substances, these substances may be resorbable or non-resorbable in vivo. The role of these substances is to fill the collapsed portions by creating volume in or under the skin, for treating different portions of the body, in particular the face. By this mechanical effect, the skin is re-tensioned and the wrinkles are smoothed, leading to a younger appearance of the treated area.

Among the so-called resorbable filling substances, mention may be made of crosslinked hyaluronic acid (HA) (also called «stabilized HA») used in dermal aesthetics. It is injected into or under the dermis in order to fill wrinkles or restore the volume of various areas of the body for a period of several months. It has the advantage of having very little secondary effects in post-injection and extremely rare complications in the long term. On the other hand, in the case of a bad injection, the practitioner has the possibility of correcting his/her treatment by injecting a solution of hyaluronidases (specific enzymes of HA), a solution which will degrade the product based on crosslinked HA which was injected beforehand. Injections of crosslinked HA, because of their gradual disappearance (resorption of the polymer in the tissues over time) have to be repeated at regular intervals, generally from 6 to 12 months, in order to maintain the efficiency of the treatment. Non-crosslinked hyaluronic acid itself has a short residence time in the skin (a half-life of less than a week), it is degraded in vivo by various factors such as radical, enzymatic, thermal and mechanical degradation. It is indeed the crosslinking which allows it to significantly increase its half-life by slowing down the degradation kinetics of hyaluronic acid according to the factors described above, thus allowing efficiency of the aesthetic treatment which may attain about 12 months.

Intensive scientific research is carried out worldwide in order to develop treatments based on hyaluronic acid having reinforced performance over time. The goal is notably to have products capable of being degraded less rapidly in order to retain an optimum aesthetic effect over a period as long as possible, while retaining a very high level of security of the injected products.

Other resorbable filling substances exist on the dermo-aesthetics market. Mention may for example be made of products containing calcium hydroxyapatite. These particles are suspended in an aqueous phase which may contain a polymer like carboxymethylcellulose, a derivative of cellulose. The products of this family are injected into or under the dermis in order to fill the wrinkles or restore the volume of various areas of the body and in particular the face. They show a high level of biocompatibility, which justifies the absence of an allergy test before injection. For these products, very few secondary effects or complications are reported and a duration of efficiency of the order of 12 months or more is observed. From the point of view of resorption, the aqueous phase is rapidly removed from the treated area and the hydroxyapatite particles are degraded and metabolized by macrophages over time.

A stimulation of the endogenous production of collagen by hydroxyapatite particles is also described for these products injected into tissues of the skin.

Unfortunately these products tend to migrate, as described in various scientific publications. This migration poses a problem since it induces premature loss of the aesthetic effect (less biomaterial at the corrected area) and may potentially induce secondary effects (the particles may notably be concentrated in certain portions more or less at a distance from the area to be treated (because of mechanical stresses to which the biomaterial is subject) and locally induce so-called hard areas.

In this context, it is important to make available to practitioners, formulations having remarkable mechanical properties adapted to injections for cosmetic and/or aesthetic purposes having an increased lifetime in the tissues, ready-to-use, and not having the drawbacks described earlier.

SUMMARY OF THE INVENTION

The invention relates to an injectable and bioresorbable sterile aqueous formulation, used for aesthetic purposes, as a particulate cohesive viscoelastic gel comprising i) cross-linked hyaluronic acid or one of its salts, at a concentration of between 0.1% and 4% (mass/volume); the molecular mass of hyaluronic acid or one of its salts, being between $2.5 \times 10^5$ Da and $4 \times 10^6$ Da, the crosslinking carried out providing the possibility of obtaining a gel based on crosslinked hyaluronic acid with a so-called cohesive structure, and ii) hydroxyapatite, at a concentration of between more than 70% and 140% (mass/volume), said hydroxyapatite being in the form of particles with an average size of less than or equal to 200 µm; said injectable sterile aqueous formulation having viscoelastic properties such that tan δ at the frequency of 1 Hz is less than or equal to 0.60.

According to another goal, the present invention relates to a method for preparing an injectable sterile aqueous formulation comprising the steps consisting of: a) preparing a first mixture comprising at least 1% to 4% by weight of cross-linked hyaluronic acid or of one of its salts, by forming covalent bonds between the chains of said biopolymer by means of bi- or poly-functional molecules, the crosslinking carried out providing the possibility of obtaining a gel based on crosslinked hyaluronic acid with a so-called cohesive structure, b) purifying said first mixture, c) then adding hydroxyapatite at a concentration comprised between 5% to 60% (mass/volume) by dispersing it homogeneously in the gel based on crosslinked hyaluronic acid, d) putting the thereby obtained gel in a ready-to-use form, e) sterilizing the product in humid heat.

Also according to another object, the present invention relates to a kit preferably in the form of a syringe containing the formulation as described earlier.

BRIEF DESCRIPTION OF THE FIGURE

FIG. 1 represents photographs of the comparison of the B', X gels, and of the formulation based on CMC and hydroxyapatite, according to the tests described in Example 2.

DETAILED DESCRIPTION OF THE INVENTION

The invention described hereafter has the goal of proposing a novel bioresorbable injectable sterile aqueous formulation used for cosmetic and aesthetic purposes and having specific properties of viscoelasticity, of filling and of long-term performance. This formulation is characterized in that it is in the form of a particular cohesive viscoelastic gel comprising
i) crosslinked hyaluronic acid, or one of its salts, at a concentration of between 0.1% and 4% (mass/volume), the crosslinking carried out providing the possibility of obtaining a gel based on crosslinked hyaluronic acid with a so-called cohesive structure, and
ii) hydroxyapatite, at a concentration of between at least 70% and 140% (mass/volume), said hydroxyapatite being in the form of particles with an average size of less than or equal to 200 µm;
said injectable sterile aqueous formulation having viscoelastic properties such that tan δ at the frequency of 1 Hz is less than or equal to 0.60.

Quite surprisingly, it was seen that this formulation has the remarkable ability to generate volume in tissues over the long term, by means of synergy between crosslinked hyaluronic acid and hydroxyapatite particles, according to the conditions of the invention.

From a mechanical point of view, the hydroxyapatite particles (with a solid behavior: strong elasticity and negligible viscosity) considerably reinforce the elasticity of the gel and therefore its ability to generate volume by inducing significant force/pressure on the tissues in order to correct the defective area to be treated.

Crosslinked hyaluronic acid itself provides viscoelasticity properties, i.e. elasticity but also viscosity with which it is possible to have gel consistency coming close to that of tissues and therefore thus compensating for the very strong elasticity and the absence of viscosity provided by the hydroxyapatite particles. This provides the possibility of having a product which is integrated into the tissues in a much more homogeneous way (the patient less feeling the product upon touching), less traumatic for tissues (strong limitation of inflammation in post-injection) and less painful upon injection.

On the other hand, crosslinked hyaluronic acid under the conditions of the invention, will allow considerable reduction in the migration of hydroxyapatite particles, particles which are retained within the gel, because of the strong cohesivity present on the account of the crosslinked hyaluronic acid of a cohesive type (crosslinked hyaluronic acid having low resorption kinetics). This strong limitation of the migration provides the possibility of having a gel with an improved volume-forming ability over the long term and able to reduce side-effects like the occurrence of so-called hard areas, felt by the patient.

Hyaluronic acid is a polysaccharide consisting of the repetition of glucuronate disaccharide and N-acetyl glucosamine units. It is widely distributed among connective, epithelial and nerve tissues in humans as well as in animals. It is one of the main components of the extracellular matrix. It significantly contributes to proliferation and to migration of the cells. It is notably found in a substantial concentration in the aqueous humor, synovial liquid, skin and the umbilical cord.

Among the preferred salts of hyaluronic acid according to the invention, mention will be made of hyaluronic acid salts with a cation, for example a mono- or di-valent salt such as a sodium, potassium, magnesium, calcium, manganese salt. Sodium salts are most particularly preferred.

According to the invention hyaluronic acid or one of its salts is in a crosslinked form. This crosslinking is obtained by forming covalent bonds between the chains of said biopolymer by means of bi- or poly-functional molecules, the crosslinking carried out providing the possibility of obtaining a gel based on crosslinked hyaluronic acid with a so-called cohesive, further called monophasic structure.

The cohesive nature of the gel based on crosslinked hyaluronic acid is a major and required specific feature of the invention. The gel should not rapidly disperse when it is introduced into also water, as would a gel with a non-cohesive nature called a "biphasic" gel (type of gel based on crosslinked hyaluronic acid which is not able to maintain the hydroxyapatite particles and therefore avoid migration). Example 2 brings out this difference between a cohesive and a non-cohesive gel.

The present invention generally comprises a concentration of crosslinked hyaluronic acid, or of one of its salts, between 0.1% and 4% (mass/volume), preferably between 0.5% and 3% or between 1% and 2% (mass/volume). According to one particularly preferred alternative, the concentration of crosslinked hyaluronic acid, or of one of its salts is between 0.9% and 1.5% (mass/volume). Alternatively, the concentration of crosslinked hyaluronic acid, or of one of its salts, may be between 1.01% and 2% (mass/volume) or between 1.1% and 1.5% (mass/volume).

Advantageously, the aqueous formulation according to the invention comprises hyaluronic acid, or one of its salts, the molecular mass of which is preferably between $2.5 \times 10^5$ Da and $4 \times 10^6$ Da, or $8 \times 10^5$ Da and $4 \times 10^6$ Da. According to a particularly preferred alternative, this molecular mass is between $1 \times 10^6$ Da and $3 \times 10^6$ Da. Alternatively, the molecular mass is preferably between $1 \times 10^6$ Da and $2.5 \times 10^6$ Da, or between $1.5 \times 10^6$ Da and $3.5 \times 10^6$ Da.

Hydroxyapatite is a mineral species from the family of phosphates, of formula $(Ca_5(PO_4)_3(OH)$, usually written as $Ca_{10}(PO_4)_6(OH)_2$ in order to underline the fact that the lattice of the crystal structure comprises two molecules. Hydroxyapatite belongs to the crystallographic family of apatites, isomorphous compounds having the same hexagonal structure. This compound has been used as a biomaterial for many years in various medical specialty products.

The present invention generally comprises a concentration of hydroxyapatite particles comprised between more than 70% and 140% (mass/volume), preferably between 71% to 135%, or 75% to 130% or 80% to 125% (mass/volume), and more preferably, between 85% to 120% or 85% to 115% or 90% to 110% or 95% to 105% (mass/volume). The average size of the hydroxyapatite particles is less than or equal to 200 µm, preferably less than 50 µm, preferably greater than 10 μm. According to one particularly preferred alternative, the average size of the hydroxyapatite particles is between 5 μm and 100 μm or 10 μm and 100 μm, or between 20 μm and 60 μm or 25 μm and 45 μm.

It has been observed that the viscosity and the elasticity properties of the formulation according to the invention are optimum when the parameter tan delta or tan δ, corresponding to the [viscosity modulus G"/elastic modulus G'] ratio at the frequency of 1 Hz, is less than or equal to 0.60, preferably less than or equal to 0.58, more preferably less than or equal to 0.50. Indeed it was shown that the elastic nature of the formulation according to the invention, relative to its viscosity, should be sufficiently large so as to be able to avoid sedimentation of the hydroxyapatite particles. Thus, it was observed that below 0.60, the hydroxyapatite particles tend to settle over time. This sedimentation involves the obtaining of a non-homogeneous formulation based on hydroxyapatite particles, which is not satisfactory for the act of injecting the formulation through a needle (blocking the needle) on the one hand and for the safety and performance of the formulation at the injection area (for example, generation of so-called hard areas in the tissues of the skin) on the other hand.

Generally, the measurement of the elasticity (G') and of the ratio of viscosity over elasticity (tan delta=G"/G') is carried out by a frequency scan from 0.01 to 100 Hz by means of a rheometer with a flat geometry of 40 mm, an air gap of 1,000 μm and an analysis temperature of 25° C.

As shown in Example 2, the cohesivity of the formulation according to the invention is a major element but it is also required that the viscoelastic nature of the latter be suitable so as to:

avoid sedimentation over time of the hydroxyapatite particles within their container, and avoid having a product which will separate into 2 phases (hydroxyapatite particles and crosslinked hyaluronic acid gel) during the injection and/or at the injection area, thereby generating heterogeneous zones in the treated area.

Another goal of the invention is to have a better lifetime as compared with formulations of the prior art. This better lifetime of the aesthetic effect is obtained through the ability of the crosslinked hyaluronic acid to maintain over the long term the hydroxyapatite particles in the injection area and the ability of the hydroxyapatite particles to impart remarkable mechanical/rheological properties over the long term. Therefore there will be less need to renew the injections with the formulation according to the invention, the gain in lifetime in a clinical situation probably being of several months.

It is also important to specify that the presence of radioopaque hydroxyapatite particles provides an advantage to the gel since they may be easily localized by the practitioner by radiography during and/or after injection.

On the other hand, the ability of the hydroxyapatite particles to stimulate the endogenous production of collagen is an important element of the invention. Slow resorption of the product in the tissues will be accompanied by production of collagen (generation of volume and elasticity), which will provide the possibility of participating in the performance of the treatment in the long term.

The possibility given to the practitioner of injecting a solution of hyaluronidases for correcting his/her injection and degrading the crosslinked hyaluronic acid making up the product also gives an advantage to the invention. This injection does not however allow acceleration of the resorption of hydroxyapatite particles: therefore there is no complete degradation of the product within the tissues.

The present invention therefore consists in a formulation, as described above, used for filling and/or restoring volumes and/or replacing biological tissues, in particular i) restoring volumes of the face (cheeks, chin, cheekbones, temples, . . . ), ii) restoring volumes of the body (buttocks, breasts, hands, . . . ), iii) restoring volumes of the face in HIV patients affected by facial lipodystrophy.

The formulation according to the invention is generally used as such but it is not excluded that at least one other additive (other than those mentioned above) and/or at least one active ingredient are added thereto.

Advantageously, the formulation according to the invention is a ready-to-use formulation, since the practitioner does not have to mix himself/herself the crosslinked hyaluronic acid and a hydroxyapatite solution, just before the injection.

Thus, the formulation may further comprise one or several ceramic materials. These materials are generally selected from the group comprising tri-calcium phosphate, calcium carbonate and calcium sulfate, or a combination of several of its ceramic materials.

The formulation according to the invention may also further comprise one or several anesthetics, selected from the group comprising lidocaine alone or in combination with adrenaline, procaine, etidocaine alone or in combination with adrenaline, articaine alone or in combination with adrenaline, mepivacaine, pramocaine, quinisocaine, or one or several of the salts of these anesthetics. According to a particularly preferred alternative, the selected anesthetic is lidocaine hydrochloride. The presence of an anesthetic in the formulation according to the invention has a major benefit for improving the comfort of the patient during and after injection.

According to another particular embodiment of the invention, the formulation according to the invention may also further comprise one or several antioxidants, such as the antioxidants of the family of polyols. The antioxidant may be selected from the group of polyols comprising sorbitol, glycerol, mannitol or propylene glycol.

According to another object, the present invention relates to a method for preparing an injectable sterile aqueous formulation according to the present invention comprising the steps: a) preparing a first mixture comprising, e.g. at least 0.1% to 4% or at least 1% to 4% by weight, of crosslinked hyaluronic acid or one of its salts, by forming covalent bonds between the chains of said biopolymer by means of bi- or poly-functional molecules, the crosslinking carried out providing the possibility of obtaining a gel based on crosslinked hyaluronic acid with a so-called cohesive structure, b) purifying said first mixture, c) then adding hydroxyapatite, e.g. to a concentration of between more than 70% and 140% (mass/volume) by dispersing it homogeneously in the gel based on crosslinked hyaluronic acid, d) converting the gel thereby obtained into a ready-to-use form, e) sterilizing the product in humid heat.

Sterilization of the formulation according to step e) is achieved in humid heat. One skilled in the art will know how to select a heat sterilization cycle (temperature and duration of the sterilization cycle) suitable for sterilizing his/her product. For example, the following sterilization cycles in humid heat may be used: 131° C., 1 min/130° C., 3 min/125° C., 7 mins/121° C., 20 mins.

According to another goal, the present invention relates to a kit preferably in the form of a syringe containing the formulation as described earlier.

The present invention also relates to a kit in the form of a container other than a syringe such as an ampoule or a flask containing the formulation as described above.

The inventor has shown that in the following examples that the formulation according to the invention based on crosslinked HA should have specific properties, notably cohesivity properties. If such is not the case (see the examples with non-crosslinked HA or with crosslinked HA not having the claimed structure), the hydroxyapatite particles are not properly maintained within the matrix and may therefore diffuse relatively easily out of the gel, which implies a loss of volume at the treated area (i.e. a loss of efficiency) and possible complications because of this migration causing safety problems.

The invention will now be illustrated in a non-limiting way with the following Examples 1 to 4:

EXAMPLES

Example 1

Preparation of a Gel Based on Crosslinked Hyaluronic Acid with a so-Called Cohesive Structure Step 1:3.5 g of sodium hyaluronate of molecular weight 2.6 MDa are added to 1% sodium hydroxide (30.5 g). The mixture is left to homogenize for 1 h 30 mins. 420 mg of butanediol diglycidyl ether (BDDE) are added to the mixture which is homogenized, closed and then placed in a water bath at 50° C. for 2 h. The mixture is then neutralized by adding 7.5 g of 1N HCl.

The gel is purified for 24 h by dialysis with an iso-osmolar physiological solution having neutral pH (regenerated cellulose, separation limit: molecular mass=60 kDa) in order to obtain a hyaluronic acid concentration of 25 mg/ml (2.5%). It is then homogenized in a conventional blade mixer for 1 h 30 mins (=gel A1/124 g).

The gel may finally be degassed, filled into 2 ml glass syringes and sterilized by a steam autoclave at 130° C. for 3 minutes (-gel A/viscoelastic gel of a so-called cohesive or monophasic structure).

Step 2: Preparation of the gel according to the invention. In 100 g of gel A1, 42.9 g of phosphocalcium hydroxyapatite $Ca_{10}(PO_4)_6(OH)_2$ are added, the particles of which have an average grain size between 30 and 50 micrometers and then the gel is homogenized in a conventional mixer with blades for 1 h 30 mins (=gel B1/142.9 g).

The gel may finally be degassed, filled into 2 ml glass syringes and sterilized by a steam autoclave at 130° C. for 3 minutes (=gel B).

The gel is particulate, cohesive, viscoelastic. Indeed, the latter appears as a viscoelastic gel (it has elasticity G' and viscosity G" properties/see below), having strong cohesivity (see Example 2) and containing hydroxyapatite particles.

The hyaluronic acid concentration of the gel is 17.5 mg/ml (1.75%) (assay with carbazole, method of the European Pharmacopeia). On the other hand, the pH (7.15) and the osmolarity (315 mOsm/kg) of the gel are physiological values.

The gel is easily injectable through a needle: A force of 26.3 N is required for pushing the gel through a 21G 1½ needle, considering a pushing rate of 12.5 mm/minute.

The gels A and B are characterized from a mechanical/rheological point of view: The rheometer used for carrying out these characterizations is a AR2000 (TA Instruments) with a flat geometry of 40 mm, an air gap of 1,000 micrometers and an analysis temperature of 25° C.

A measurement of the elasticity (G') and of the ratio of viscosity over elasticity (tan delta=G"/G') is carried out by using a frequency scan from 0.1 to 100 Hz.

A comparison of the parameters is carried out at 1 Hz.

| Gel | G'(1 Hz) in Pa | Tan delta (1 Hz) |
|-----|----------------|------------------|
| A   | 184            | 0.25             |
| B   | 381            | 0.29             |

It is seen that the product B has a significantly higher elasticity than the product A. The tan delta values of each of the products A and B, however, are relatively close: the gel B retains a substantially viscous nature, in spite of the presence of the hydroxyapatite particles (which themselves have high elasticity and negligible viscosity). This stronger elasticity, in combination with the strong cohesivity of the product according to the invention, provides an enhanced ability of the product to generate volume in tissues.

A measurement of the normal force induced by the gel to be tested is carried out by compressing the sample between the Peltier plane and the geometry for an air gap of 1,500 micrometers and an amount of gel of 1.4 g.

| Gel | Normal force (N) |
|-----|------------------|
| A   | 0.86             |
| B   | 1.47             |

It may be seen that the product B has a significantly stronger elasticity and induced normal force than the product A.

This stronger elasticity, combined with the strong cohesivity of the gel according to the invention, provides an enhanced ability of the product to generate volume in tissues.

Example 2

Importance of the so-Called Cohesive Structure of the Gel Based on Corsslinked HA—Comparison The gel A1 (of a so-called cohesive or monophasic structure) described in Example 1 is dialyzed with an iso-osmolar physiological solution having neutral pH (regenerated cellulose, separation limit: molecular mass=60 kDa) in order to obtain a hyaluronic acid concentration of 20 mg/ml (2%).

Calcium hydroxyapatite is then added into the gel in order to obtain a concentration of 200 mg/ml (20%) and then mixing with a spatula is carried out (2 minutes for 5 g of gel).

The gel thereby obtained is then sterilized in the autoclave at 121° C. for 20 minutes (=gel B' according to the invention).

The commercial Resylane® Perlane® gel (batch 11363-1) based on crosslinked hyaluronic acid with a non-cohesive or biphasic structure, the hyaluronic acid concentration of which is 20 mg/ml (2%), is doped with 200 mg/ml (20%) of calcium hydroxyapatite by mixing with a spatula (2 minutes for 5 g of gel).

The gel thereby obtained is then sterilized in the autoclave at 121° C. for 20 minutes (=gel X).

The gel A1 and the Restylane® Perlane® gel are compared according to the following test:

In 30 ml flasks containing 5 ml of purified water, 1 ml of gel A1 is introduced into the flask 1 and 1 ml of Restylane® Perlane® gel is introduced into the flask 2. After closing the flasks, both flasks are mixed manually for 5 seconds.

After 10 seconds, it is observed that the Restylane® Perlane® gel has completely disaggregated/dispersed, forming a multitude of particles in the aqueous solution. Thus the Restylane® Perlane® gel does indeed have a so-called non-cohesive or biphasic structure (the gel is rapidly dispersed in the aqueous solution).

The gel A1, however, is always in the form of a «gel ball» in the aqueous solution. It therefore indeed has a so-called cohesive or monophasic structure (the gel does not rapidly disperse in the aqueous solution, it has strong cohesivity, unlike the Restylane®Perlane® gel).

The gel B' according to the invention and the gel X are compared according to the following test (see FIG. 1):

In a 30 ml plastic flask containing 5 ml of purified water, 1 ml of gel B' is introduced into the flask 1 and 1 ml of gel X into the flask 2. After closing the flasks, both flasks are mixed for 5 seconds, manually.

After 10 seconds, it is observed that the gel X has completely disaggregated/dispersed, forming a multitude of particles in the aqueous solution. The gel X has a particulate non-cohesive viscoelastic structure. It does not correspond to the characteristics of the gel according to the invention. In medical practice for a use in aesthetics, the latter will diffuse/migrate around the injection area.

The gel B', itself, is always in the form of a gel ball in the aqueous solution. It therefore indeed has a particulate cohesive structure which within the scope of medical practice for use in aesthetics will give the possibility of not diffusing/migrating around the injected area, and thus avoiding complications related to the migration of hydroxyapatite particles in the tissues but also having better long term performance of the product since the injected gel will be able to maintain its ability to generate volume in tissues over a long period, in view of the absence of migration of the biomaterial of the treated area.

Example 3

Importance of the Viscoelasticity of the Gel according to the Invention—Comparison Let C be a gel prepared according to the same procedure (Steps 1&2) as the one described in Example 1 by introducing 200 mg of BDDE instead of 420 mg.

Let D be a gel prepared according to the same procedure (Steps 1&2) as the one described in Example 1 by introducing 290 mg of BDDE instead of 420 mg.

The gel C is characterized from a mechanical/rheological point of view.

The rheometer used for carrying out the rheological characterizations is an AR2000 (TA Instruments) with a flat geometry of 40 mm, an air gap of 1,000 micrometers and an analysis temperature of 25° C.

A measurement of the viscosity-to-elasticity ratio (tan delta=G"/G') is carried out by performing frequency scanning from 0.01 to 100 Hz.

A comparison of the parameters is carried out at 1 Hz.

| Gel | Tan delta = G"/G'(1 Hz) |
|---|---|
| C | 0.84 |
| D | 0.58 |

It is seen that the hydroxyapatite particles tend to settle over time (a phenomenon which is well observed when a sample is transferred to the centrifuge) for gel C, which is not observed for gel D.

This sedimentation involves obtaining products based on non-homogeneous hydroxyapatite particles, which is not satisfactory for the act of injecting the gel through a needle (blocking of the needle) but also for the safety and the performance of the product in the injection area (significant risks of complications such as for example the generation of so-called hard areas in the tissues of the skin).

As shown in the Example 2 the cohesivity of the gel according to the invention is significant but it is also required that the viscoelastic nature of the latter be suitable so as to:

avoid sedimentation over time of the hydroxyapatite particles within their container, avoid having a product which will separate into 2 phases (hydroxyapatite particles and crosslinked hyaluronic acid gel) during the injection and/or at the injection area, thereby generating heterogeneous zones in the treated area.

The elastic nature of the gel (relative to its viscosity) should therefore be sufficiently large so as to be able to avoid sedimentation of the particles.

Example 4

Comparison of the Gel According to the Invention with Solution of the Prior Art
a) Formulation Based on Non-Crosslinked HA and on Hydroxypatite.

As described in the literature, in vivo, non-crosslinked hyaluronic acid has a lifetime of less than one week.

Therefore, a non-crosslinked HA solution with hydroxyapatite is of no interest since the non-crosslinked hyaluronic acid will be very rapidly resorbed and it will not allow migration of the hydroxyapatite particles to be prevented over the long term.
b) Aqueous Formulation of Hydroxyapatite.

An aqueous solution of hydroxyapatite (S1) is prepared (30% of phosphocalcium hydroxyapatite having a grain size comprised between 30 and 50 micrometers in an iso-osmolar physiological solution and having neutral pH).

In a 30 ml plastic flask containing 5 ml of purified water, 1 ml of solution S1 is introduced. Immediate dispersion of the hydroxyapatite particles in the flask is observed.

Unlike the formulation according to the invention, the solution S1 is unable to maintain the hydroxyapatite particles at the injection area over the long term.
c) Formulation Based on CMC and Hydroxyapatite (See FIG. 1)

An aqueous formulation of carboxymethylcellulose (CMC) and of hydroxyapatite (S3) is prepared (30% of phosphocalcium hydroxyapatite having a grain size comprised between 30 and 50 micrometers, and 2% of CMC at 250,000 Da in an iso-osmolar physiological solution having a neutral pH).

In a 30 ml plastic flask containing 5 ml of purified water, 1 ml of the formulation S3 is introduced. After closing the flask, the flask is manually mixed for 5 seconds.

After 10 seconds, it is observed that the formulation S3 is completely disaggregated/dispersed as a multitude of particles in the aqueous solution.

Unlike the formulation according to the invention, the formulation S3 is unable to maintain the hydroxyapatite particles in the injection area over the long term.

The invention claimed is:
1. An injectable sterile aqueous formulation in the form of a particulate cohesive viscoelastic gel comprising:
  i) crosslinked hyaluronic acid, or a salt thereof, at a concentration of between 0.1% and 4% (mass/volume), and
  ii) hydroxyapatite at a concentration of between more that 70% and 140% (mass/volume), the hydroxyapatite being in the form of particles with an average size of less than or equal to 200 µm, wherein the injectable sterile aqueous formulation exhibits viscoelastic properties such that the tan δ at a frequency of 1 Hz is less than or equal to 0.60.

2. The injectable sterile aqueous formulation of claim 1, wherein the molecular mass of the hyaluronic acid, or of one of its salts, is between $2.5 \times 10^5$ Dalton (Da) and $4 \times 10^6$ Da.

3. The injectable sterile aqueous formulation of claim 1, wherein the formulation has been sterilized in humid heat.

4. The injectable sterile aqueous formulation of claim 1, wherein the concentration of the crosslinked hyaluronic acid or of one of its salts, is between 0.5% and 2% (mass/volume).

5. The injectable sterile aqueous formulation of claim 1, wherein the concentration of hydroxyapatite is between 75% and 120% (mass/volume).

6. The injectable sterile aqueous formulation of claim 1, wherein the concentration of hydroxyapatite is between 80% and 110% (mass/volume).

7. The injectable sterile aqueous formulation of claim 1, wherein the average size of the hydroxyapatite particles is less than or equal to 100 µm and greater than or equal to 10 µm.

8. The injectable sterile aqueous formulation of claim 1, wherein the average size of the hydroxyapatite particles is less than or equal to 50 µm and greater than or equal to 10 µm.

9. The injectable sterile aqueous formulation of claim 1, wherein the formulation further comprises one or more ceramic materials.

10. The injectable sterile aqueous formulation of claim 1, wherein the formulation further comprises one or more anaesthetics.

11. The injectable sterile aqueous formulation of claim 10, wherein the one or more anaesthetics are selected from the group consisting of lidocaine, adrenaline, procaine, etidocaine, articaine, mepivacaine, pramocaine, quinisocaine, and salts thereof.

12. The injectable sterile aqueous formulation of claim 11, wherein the anaesthetic is lidocaine hydrochloride.

13. The injectable sterile aqueous formulation of claim 1, wherein the formulation further comprises one or more antioxidants.

14. The injectable sterile aqueous formulation of claim 13, wherein the one or more antioxidants are polyols.

15. The injectable sterile aqueous formulation of claim 14, wherein the polyols are selected from the group consisting of sorbitol, glycerol, mannitol and propylene glycol.

16. The injectable sterile aqueous formulation of claim 1, which is in the form of an aesthetic filler for filling and/or restoring volumes and/or replacing biological tissues.

17. A kit containing the injectable sterile aqueous formulation of claim 1.

18. The kit of claim 17, wherein the injectable sterile aqueous formulation is comprised in a syringe, an ampoule or a flask.

19. A method for making an injectable sterile aqueous formulation according to claim 1 comprising the steps:
  a) preparing a first mixture comprising crosslinked hyaluronic acid, or a salt thereof, by forming covalent bonds between the chains of the hyaluronic acid using bi- or poly-functional molecules to provide a crosslinked hyaluronic acid with a cohesive structure,
  b) purifying the first mixture,
  c) adding hydroxyapatite to the purified first mixture from step b) and dispersing the hydroxyapatite homogeneously in the purified first mixture comprising crosslinked hyaluronic acid to form a gel product,
  d) converting the gel product obtained in step c) into a ready-to-use form, and
  e) sterilizing the gel product in a ready-to-use form in humid heat.

* * * * *

UNITED STATES PATENT AND TRADEMARK OFFICE
CERTIFICATE OF CORRECTION

PATENT NO. : 10,434,040 B2
APPLICATION NO. : 15/941735
DATED : October 8, 2019
INVENTOR(S) : Samuel Gavard Molliard Page 1 of 1

It is certified that error appears in the above-identified patent and that said Letters Patent is hereby corrected as shown below:

On the Title Page

Column 2, under OTHER PUBLICATIONS, Line 3: "PCT/EP"20131069874" should read -- PCT/EP"2013/069874 --

Signed and Sealed this
Nineteenth Day of November, 2019

Andrei Iancu
*Director of the United States Patent and Trademark Office*